United States Patent [19]

Goletz et al.

[11] Patent Number: 5,196,407
[45] Date of Patent: Mar. 23, 1993

[54] COMPOSITION FOR PRESERVING WOOD AND WOOD MATERIALS

[75] Inventors: Peter Goletz, Kempen Sankt Hubert; Luzian Naczinski, Meerkamp-Lank, both of Fed. Rep. of Germany

[73] Assignee: Desowag Materialschutz GmbH, Duesseldorf, Fed. Rep. of Germany

[21] Appl. No.: 703,093

[22] Filed: May 22, 1991

[30] Foreign Application Priority Data

May 23, 1990 [DE] Fed. Rep. of Germany ....... 4016601
May 23, 1990 [DE] Fed. Rep. of Germany ....... 4016602

[51] Int. Cl.$^5$ .................. A01N 37/34; A01N 43/64; A01N 47/10; A01N 55/00
[52] U.S. Cl. ........................... 514/63; 424/78; 424/81; 514/383; 514/478; 514/479; 514/521; 514/531
[58] Field of Search .............. 514/478, 479, 383, 63, 514/521, 531; 424/78, 81

[56] References Cited

FOREIGN PATENT DOCUMENTS 2072505 2/1981 United Kingdom .

Primary Examiner—Allen J. Robinson
Attorney, Agent, or Firm—Foley & Lardner

[57] ABSTRACT

An aqueous composition for preserving wood and wood materials comprising a fungicide selected from the group consisting of 1-[[2-(,4dichlorophenyl-4-propyl-1,3-dioxolan-2-yl]methyl]-1H-1,2,4- triazole, (common name propiconazol) and α-[[2-(4-chlorophenyl)ethyl]-α-(1,1-dimethylethyl)-1H-1,2,4-triazol-1-ethanol; a fungicidal carbamate; namely 3-iodo-2-propynylbutyl carbamate or methyl benzimidazol-2-ylcarbamate; a stabilizer, 2,2,4-trimethyl-1,3-pentadiol monoisobutyrate, and a diluent. The composition can optionally comprise an insecticide, an emulsifier, a wetting agent and an organic-chemical binder or fixing agent.

21 Claims, No Drawings

COMPOSITION FOR PRESERVING WOOD AND WOOD MATERIALS

BACKGROUND OF THE INVENTION

The present invention relates to an aqueous composition for preserving wood and wood materials, comprising a combination of fungicides, a stabilizer and a diluent, and optionally, an insecticide, an emulsifier, a wetting agent and an organic-chemical binder or fixing agent.

DE-OS 3,004,319 discloses wetting agent wood preservative concentrates containing insecticides selected from the group consisting of carbamates, phosphates, thiophosphates, thionophosphates, chlorinated hydrocarbons and pyrethroids, and fungicides selected from the group consisting of tetravalent organotin compounds, chlorinated phenols, triazols, N-cyclohexyl-diazeniumdioxyaluminum as well as N,N-dimethyl-N'-phenyl-N'-(fluorodichloromethylthio)sulfamide. The wood preservatives disclosed in the '319 patent, however, do not contain stabilizing agents.

European Patent Application 0,040,106 discloses aqueous wood preservatives containing the fungicidal carbamate, 3-iodo-2-propynylbutylcarbamate. Tests carried out by the applicant, however, revealed that the stability of the active substance was unsatisfactory because solvents and aromatic and aliphatic hydrocarbons such as glycols caused a decrease in the stability of the active substance in the presence of water.

A need therefore continues to exist for a wood preserving composition having stabilizing agents which improve the stability of the active agents of the wood preserving composition.

Applicant has surprisingly found that the concomitant use according to the invention of 2,2,4-trimethyl-1,3-pentadiol monoisobutyrate improves the stability of the active substances of the wood preserving composition according to the invention in polar and nonpolar organic-chemical solvents and solvent mixtures.

Applicant has also surprisingly found that the concomitant use according to the invention of 2,2,4-trimethyl-1,3-pentadiol monoisobutyrate provides improved distribution of the active substances of the wood preserving composition in the wood to be preserved.

OBJECTS OF THE INVENTION

It is an object of the present invention to provide an aqueous composition for preserving wood and wood materials having good activity against wood-discoloring fungi and wood-destroying insects as well as good stabilization of the active substances in the aqueous formulations due to the selection of very particular fungicides and insecticides as well as the selection of appropriate stabilizing agents.

Another object of the invention is to provide an aqueous composition for preserving wood and wood materials not only having improved anti-fungal and anti-insecticidal properties, but also an aqueous composition having improved penetration of the active substances into the wood as well as uniform distribution of the active substances in the wood itself.

SUMMARY OF THE INVENTION

These and other objects of the invention are achieved by a first embodiment of the invention which provides an aqueous composition for preserving wood and wood materials comprising:

(a) a first fungicide ranging from about 0.1 to about 2.0% by weight of said composition wherein said first fungicide is selected from the group consisting of α-[[2-(4-chlorophenyl)ethyl]-α-(1,1-dimethylethyl)-1H-1,2,4-triazol-1-ethanol and 1-[[2-(2,4-dichlorophenyl-4-propyl-1,3dioxolan-2-yl}-methyl}-1H-1,2,4-triazole;

(b) a second fungicide, said fungicide being a fungicidal carbamate ranging from about 0.2 to about 2.3% by weight of said composition wherein said second fungicide is selected from the group consisting of 3-iodo-2-propynylbutyl carbamate and methyl benzimidazol-2-ylcarbamate;

(c) a stabilizer ranging from about 1.0 to about 5.0% by weight of said composition wherein said stabilizer is 2,2,4-trimethyl-1,3-pentadiol monoisobutyrate; and (d) a diluent comprising at least about 89% by weight of said composition.

Another embodiment of the invention further provides an aqueous composition for preserving wood and wood products comprising:

(a) a first fungicide ranging from about 0.1 to about 2.0% by weight of said composition wherein said first fungicide is selected from the group consisting of α-[[2-(4-chlorophenyl)ethyl]-α-(1,1-dimethylethyl)-1H-1,2,4-triazol-1-ethanol and 1-[[2-(2,4-dichlorophenyl-4-propyl-1,3-dioxo)an-2-yl}methyl}-1H-1,2,4-triazole; and (b) a second fungicide, said second fungicide being a fungicidal carbamate ranging from about 0.2 to about 2.3% by weight of said composition wherein said second fungicide is selected from the group consisting of 3-iodo-2-propynylbutyl carbamate and methyl benzimidazol-2-ylcarbamate;

(c) an insecticide ranging from about 0.002 to about 0.8% by weight of said composition, said insecticide selected from the group consisting of cyano-(4-fluoro-3-phenoxyphenyl)methyl-3-(2,2-dichloroethenyl)-2,2 -dimethylcyclopropanecarboxy-late, (±)α-cyano-3-phenoxybenzyl(±)-cis,trans-3-(2,2-dichlorovinyl)-2,2-dimethylcyclopropanecarboxylate,(S)-α-cyano-3-phenoxybenzyl(1R,3R)-3-(2,2-dibromovinyl)-2,2-dimethylcyclopropanecarboxylate and 3-phenoxybenzyl (±)-cis,trans-3-(2,2-dichlorovinyl)-2,2-dimethylcyclopropanecarboxylate;

(d) a stabilizer ranging from about 1.0 to about 5.0% by weight of said composition wherein said stabilizer is 2,2,4-trimethyl-1,3-pentadiol monoisobutyrate; and (e) a diluent comprising at least about 89% by weight of said composition.

DETAILED DESCRIPTION OF THE PREFERRED EMBODIMENTS

The aqueous composition according to the invention described at the outset, for preserving wood and wood materials, contains 0.1 to 2.0% by weight, preferably 0.8 to 1.5% by weight, of either 1-[[2-(,4-dichlorophenyl-4-propyl-1,3-dioxolan-2-yl]methyl]-1H-1,2,4-triazole, (common name propiconazol) or α-[[2-(4-chlorophenyl)ethyl]-α-(1,1-dimethylethyl)-1H-1,2,4-triazol-1-ethanol (common name: tebuconazol), 0.2 to 2.3% by weight, preferably 0.3 to 1.2% by weight, of a fungicidal carbamate, namely 3-iodo-2-propynylbutyl carbamate or methyl benzimidazol-2-ylcarbamate, 1.0 to 5.0% by weight, preferably 2.0 to 3.0% by weight, of 2,2,4- trimethyl-1,3-pentadiol monoisobutyrate, and more than 89% by weight, preferably more than 96% by weight, of a diluent, and optionally containing an insecticide, an emulsifier, wetting agent, binder, and/or fixing agent.

In a preferred embodiment, the wood preservative according to the invention additionally contains 0.002 to 0.8% by weight, preferably 0.03 to 0.2% by weight, of the following pyrethroids: cyano-(4-fluoro-3-phenoxyphenyl)methyl-3-(2,2-dichloroethenyl)-2,2-dimethylcyclopropanecarboxylate (common name: cyfluthrin), ($\pm$)α-cyano-3-phenoxybenzyl ($\pm$)-cis,trans-3-(2,2-dichlorovinyl)-2,2-dimethylcyclopropanecarboxylate, (S)-α-cyano-3-phenoxybenzyl(1R,3R)-3-(2,2-dibromovinyl)-2,2-dimethylcyclopropanecarboxylate or 3-phenoxybenzyl ($\pm$)-cis,trans-3-(2,2-dichlorovinyl)-2,2-dimethylcyclopropanecarboxylate, (S)-α-cyano-3-phenoxybenzyl(1R,3R)-3-(2,2-dibromovinyl)-2,2-dimethylcyclopropanecarboxylate or 3-phenoxybenzyl ($\pm$)-cis,trans-3-(2,2-dichlorovinyl)-2,2-dimethylcyclopropanecarboxylate (common name: permethrin). Also included are the enantiomeric compounds of the aforementioned pyrethroids.

In a particularly preferred embodiment, the pyrethroid in the wood preservative according to the invention is replaced completely or in part by the same amounts by weight, based on 100% by weight of pyrethroid employed, of an insecticide based on organosilicon compounds, preferably by dimethyl(phenyl)silylmethyl 3-phenoxybenzyl ether or dimethyl(phenyl)silylmethyl 2-phenoxy-6-pyridylmethyl ether.

The dimethyl(phenyl)silylmethyl 3-phenoxybenzyl ether which is preferably used is dimethyl(4-ethoxyphenyl)silylmethyl 3-phenoxybenzyl ether, of the following formula

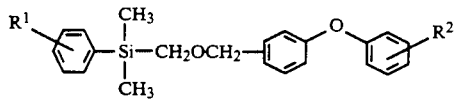

where $R^1 = 4-OC_2H_5$ and $R^2 = H$, and the dimethyl(phenyl)silylmethyl 2-phenoxy-6-pyridyl-methyl ether preferably used is dimethyl(4-ethoxyphenyl)-silylmethyl 2-phenoxy-6-pyridylmethyl ether, of the following formula

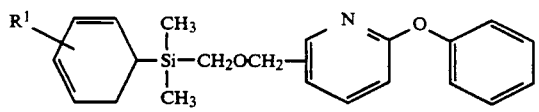

where $R^1 = 4-OC_2H_5$.

The diluent used according to the invention consists of a nonpolar or polar organic-chemical solvent or solvent mixture, preferably an oily or oil-type, slow-evaporating organic-chemical solvent or solvent mixture. Examples of the latter solvents which must be mentioned are aromatic or aliphatic hydrocarbons as well as mixtures of these, or testing gasoline.

The binder employed according to the invention is an alkyd resin and/or a dry vegetable oil, but preferably a synthetic resin based on a methyl acrylate/n-butyl acrylate copolymer, a styrene/acrylic ester copolymer and/or a polyvinyl versatate.

The use of the synthetic resins which are finely dispersed in water and which are based on the methyl acrylate/n-butyl acrylate copolymer, styrene/acrylic ester copolymer or polyvinyl versatate, the copolymers or polymers having an average particle size of less than 0.07 μm, results in preventing the biocidal active substances from remigrating from the wood to the wood surface.

The emulsifiers employed are alkylaryl sulfonates, derivatives of alkylarylsulfonic acid and/or polyoxyethylene derivatives and/or polyalkylene ethers or polyalkyl glycol ethers, preferably a surface-active organic-chemical compound containing one or more polyoxyethylene groups and/or one or more fatty acid groups.

Examplary Formulations According to the Invention

EXAMPLE 1

| | |
|---|---|
| 19.0% | alkyd resin (solid) |
| 0.5% | solvent (mixture of aromatic hydrocarbons) |
| 3.1% | emulsifier (ethoxylated nonylphenol) |
| 2.0% | 2,2,4-trimethyl-1,3-pentadiol monoisobutyrate |
| 0.8% | 3-iodo-2-propynylbutyl carbamate |
| 1.5% | tebuconazol |
| 0.05% | permethrin 48:52 |
| 73.05% | water |
| 100% | |

EXAMPLE 2

| | |
|---|---|
| 19.0% | alkyd resin (solid) |
| 0.5% | solvent (mixture of aromatic hydrocarbons) |
| 3.1% | emulsifier (ethoxylated nonylphenol) |
| 2.0% | 2,2,4-trimethyl-1,3-pentadiol monoisobutyrate |
| 0.8% | tebuconazol |
| 0.5% | methyl benzimidazol-2-ylcarbamate |
| 0.05% | permethrin 48:52 |
| 74.05% | water |
| 100% | |

EXAMPLE 3

| | |
|---|---|
| 8.0% | styrene/acrylic ester copolymer (solid) |
| 1.6% | solvent (mixture of aromatic and aliphatic hydrocarbons) |
| 3.0% | 2,2,4-trimethyl-1,3-pentadiol monoisobutyrate |
| 1.5% | tebuconazol |
| 0.8% | 3-iodo-2-propynylbutyl carbamate |
| 0.05% | permethrin 48:52 |
| 85.05% | water |
| 100% | |

EXAMPLE 4

| | |
|---|---|
| 4.0% | methacrylate/n-butyl acrylate copolymer (solid) + polyvinyl versatate (solid) |
| 1:6% | solvent (mixture of aliphatic hydrocarbons) |
| 3.0% | 2,2,4-trimethyl-1,3-pentadiol monoisobutyrate |
| 0.8% | tebuconazol |
| 0.5% | methyl benzimidazol-2-ylcarbamate |
| 0.05% | permethrin 48:52 |
| 90.05% | water |
| 100% | |

EXAMPLE 5

| | |
|---|---|
| 19.0% | alkyd resin (solid) |
| 0.5% | solvent (mixture of aromatic hydrocarbons) |
| 3.1% | emulsifier (ethoxylated nonylphenol) |
| 2.0% | 2,2,4-trimethyl-1,3-pentadiol monoisobutyrate |
| 0.8% | 3-iodo-2-propynylbutyl carbamate |
| 1.5% | tebuconazol |
| 73.8% | water |
| 100% | |

EXAMPLE 6

| | |
|---|---|
| 19.0% | alkyd resin (solid) |
| 0.5% | solvent (mixture of aromatic hydrocarbons) |
| 3.1% | emulsifier (ethoxylated nonylphenol) |
| 2.0% | 2,2,4-trimethyl-1,3-pentadiol monoisobutyrate |
| 0.8% | tebuconazol |
| 0.5% | methyl benzimidazol-2-ylcarbamate |
| 74.1% | water |
| 100% | |

EXAMPLE 7

| | |
|---|---|
| 8.0% | styrene/acrylic ester copolymer (solid) |
| 1.6% | solvent (mixture of aromatic and aliphatic hydrocarbons) |
| 3.0% | 2,2,4-trimethyl-1,3-pentadiol monoisobutyrate |
| 1.5% | tebuconazol |
| 0.8% | 3-iodo-2-propynylbutyl carbamate |
| 85.1% | water |
| 100% | |

EXAMPLE 8

| | |
|---|---|
| 4.0% | methacrylate/n-butyl acrylate copolymer (solid) + polyvinyl versatate (solid) |
| 1.6% | solvent (mixture of aliphatic hydrocarbons) |
| 3.0% | 2,2,4-trimethyl-1,3-pentadiol monoisobutyrate |
| 1.0% | tebuconazol |
| 0.5% | methyl benzimidazol-2-ylcarbamate |
| 89.9% | water |
| 100% | |

EXAMPLE 9

| | |
|---|---|
| 19.0% | alkyd resin (solid) |
| 0.5% | solvent (mixture of aromatic hydrocarbons) |
| 3.1% | emulsifier (ethoxylated nonylphenyl) |
| 2.0% | 2,2,4-trimethyl-1,3-pentadiol monoisobutyrate |
| 0.8% | 3-iodo-2-propynylbutyl carbamate |
| 0.8% | propiconazol |
| 0.05% | permethrin 48:52 |
| 73.75% | water |
| 100% | |

EXAMPLE 10

| | |
|---|---|
| 19.0% | alkyd resin (solid) |
| 0.5% | solvent (mixture of aromatic hydrocarbons) |
| 3.1% | emulsifier (ethoxylated nonylphenol) |
| 2.0% | 2,2,4-trimethyl-1,3-pentadiol monoisobutyrate |
| 0.8% | propiconazol |
| 0.5% | methyl benzimidazol-2-ylcarbamate |
| 0.05% | permethrin 48:52 |
| 74.05% | water |
| 100% | |

EXAMPLE 11

| | |
|---|---|
| 8.0% | styrene/acrylic ester copolymer (solid) |
| 1.6% | solvent (mixture of aromatic and aliphatic hydrocarbons) |
| 3.0% | 2,2,4-trimethyl-1,3-pentadiol monoisobutyrate |
| 1.5% | propiconazol |
| 0.8% | 3-iodo-2-propynylbutyl carbamate |
| 0.05% | permethrin 48:52 |
| 85.05% | water |
| 100% | |

EXAMPLE 12

| | |
|---|---|
| 4.0% | methacrylate/n-butyl acrylate copolymer (solid) + polyvinyl versatate (solid) |
| 1.6% | solvent (mixture of aliphatic hydrocarbons) |
| 3.0% | 2,2,4-trimethyl-1,3-pentadiol monoisobutyrate |
| 1.0% | propiconazol |
| 0.5% | methyl benzimidazol-2-ylcarbamate |
| 0.005% | permethrin 48:52 |
| 90.05% | water |
| 100% | |

EXAMPLE 13

| | |
|---|---|
| 19.0% | alkyd resin (solid) |
| 0.5% | solvent (mixture of aromatic hydrocarbons) |
| 3.1% | emulsifier (ethoxylated nonylphenol) |
| 2.0% | 2,2,4-trimethyl-1,3-pentadiol monoisobutyrate |
| 0.8% | 3-iodo-2-propynylbutyl carbamate |
| 0.8% | propiconazol |
| 73.8% | water |
| 100% | |

EXAMPLE 14

| | |
|---|---|
| 19.0% | alkyd resin (solid) |
| 0.5% | solvent (mixture of aromatic hydrocarbons) |
| 3.1% | emulsifier (ethoxylated nonylphenol) |
| 2.0% | 2,2,4-trimethyl-1,3-pentadiol monoisobutyrate |
| 0.8% | propiconazol |
| 0.5% | methyl benzimidazol-2-ylcarbamate |
| 74.1% | water |
| 100% | |

EXAMPLE 15

| | |
|---|---|
| 8.0% | styrene/acrylic ester copolymer (solid) |
| 1.6% | solvent (mixture of aromatic and aliphatic hydrocarbons) |
| 3.0% | 2,2,4-trimethyl-1,3-pentadiol monoisobutyrate |
| 1.5% | propiconazol |
| 0.8% | 3-iodo-2-propynylbutyl carbamate |
| 85.1% | water |
| 100% | |

EXAMPLE 16

| | |
|---|---|
| 4.0% | methacrylate/n-butyl acrylate copolymer (solid) + polyvinyl versatate (solid) |
| 1.6% | solvent (mixture of aliphatic hydrocarbons) |
| 3.0% | 2,2,4-trimethyl-1,3-pentadiol monoisobutyrate |
| 1.0% | propiconazol |
| 0.5% | methyl benzimidazol-2-ylcarbamate |
| 89.9% | water |
| 100% | |

Demonstration of the Activity of the Wood Preservative According to the Invention Against Attack By Blue Stain

| | |
|---|---|
| Testing method: | Screening of wood protectants against blue-stain fungi |
| Spore suspension: | Preparation of a spore suspension in accordance with EN 152, Part 1, Appendix B |
| Test fungi: | *Aureobasidium pullulans* *Sclerophoma pityophyla* |
| Test containers: | Kolle flasks |
| Test wood: | Pine sapwood, 3-8 annual rings/cm, planed smooth; dimensions: 9.3 × 4.5 × 1.0 cm. In the middle of the boards and at right angles to the grain, a notch of 3 mm depth and width is sawn. |
| Test procedure: | One half of the boards in each case is painted with the amount of protecting agent to be tested. The pieces of wood are subsequently stored in the laboratory for three weeks for drying. For the fungal test, each individual board is placed on a filter paper disk in a Kolle flask, and the flasks are sealed with gauze and sterilized. The spore suspension is subsequently placed on the filter in an environment which is as sterile as possible. |
| Test criterion: | After a test period of eight weeks, the degree of surface blueing and the depth of the zone which is free from blue stain is determined spearately on the "test" and "control" halves, where the figures denote: |
| | 0 = no growth of blue stain |
| | 1 = not more than 10% of the area covered in blue stain |
| | 2 = not more than 50% of the area covered with blue stain |
| | 3 = surface virtually completely covered with blue stain, or slight growth visible |
| | 4 = surface completely covered in blue stain |

The surfaces should be free from blue stain and the depth of action should reach not less than 1 mm and 1.5 mm on average.

All the compositions which follow have successfully withstood two weeks' exposure to light in the Xeno test apparatus:

Examples According to the Invention

| | Blue stain of surface | Depth of action in mm |
|---|---|---|
| Example 1 | 0 | 1.5-3.0 |
| Example 2 | 0 | 1.5-2.5 |
| Example 3 | 0 | 2.0-3.0 |
| Example 4 | 0 | 1.5-3.0 |
| Example 5 | 0 | 1.5-3.0 |
| Example 6 | 0 | 2.0-3.0 |
| Example 7 | 0 | 1.5-3.0 |
| Example 8 | 0 | 1.5-2.5 |
| Example 9 | 0 | 1.5-3.0 |
| Example 10 | 0 | 1.5-2.5 |
| Example 11 | 0 | 2.0-3.0 |
| Example 12 | 0 | 1.5-3.0 |
| Example 13 | 0 | 1.5-3.0 |
| Example 14 | 0 | 2.0-3.0 |
| Example 15 | 0 | 1.5-3.0 |
| Example 16 | 0 | 1.5-2.5 |

Detection of the Activity of the Wood Preservative According to the Invention Against Wood-Destroying Insects Number of European Test Standard DIN EN 46 "Determination of the preventive action against recently hatched larvae of *Hylotrupes bajulus* (Linnaeus). (Laboratory method)"

Composition of the Wood Preservative According to the Invention

| | |
|---|---|
| 0.05% | permethrin 48:52 |
| 1.50% | tebuconazol |
| 19.00% | alkyd resin (solid) |
| 0.80% | 3-iodo-2-propynylbutyl carbamate |
| 2.0% | 2,2,4-trimethyl-1,3-pentadioliso-butyrate |
| 3.0% | emulsifier |
| 73.65% | water |

Type of wood used:
Pine (Pinus sylvestris L.)
Test concentration of the wood preservative:
100%
Nature and number of the steps carried out:
Pipetting, 2×
Uptake of solvent or protecting agent:
See Table below
Drying method:
In accordance with DIN EN 46
Test results:
See Table below

| Type of test wood | Test concentration % | UPTAKE Solution per wood sample g | Protective agent per wood sample g/m² | LARVAE RECOVERED Dead No boring Number | Alive boring Number | Alive boring Number | Unrecovered larvae Number |
|---|---|---|---|---|---|---|---|
| Treated | 100 | | 160 | 10 | 0 | 0 | 0 |
| | 100 | | 160 | 10 | 0 | 0 | 0 |
| | 100 | | 160 | 10 | 0 | 0 | 0 |
| Untreated control | — | — | — | 0 | 0 | 10 | 0 |
| | — | — | — | 0 | 0 | 10 | 0 |
| Solvent control | — | — | — | — | — | — | — |

Detection of the Activity of the Wood Preservative According to the Invention Against Wood-Destroying Insects Number of European Test Standard DIN EN 46 "determination of the preventive action against recently hatched larvae of *Hylotrupes bajulus* (Linnaeus). (Laboratory method)"

Composition of the Wood Preservative According to the Invention

| 0.05% | permethrin 48:52 |
|---|---|
| 1.50% | propiconazol |
| 19.00% | alkyd resin (solid) |
| 0.80% | 3-iodo-2-propynyl-butyl carbamate |
| 2.0% | 2,2,4-trimethyl-1,3-pentadiolisobutyrate |
| 3.0% | emulsifier |
| 73.65% | water |

Type of wood used:
Pine (Pinus sylvestris L.)
Test concentration of the wood preservative:
100%
Nature and number of the steps carried out:
Pipetting, 2×
Uptake of solvent or protecting agent:
See Table below
Drying method:
In accordance with DIN EN 46
Test results:
See Table below.

| Type of test wood | Test concentration % | UPTAKE Solution per wood sample g | Protective agent per wood sample g/m² | LARVAE RECOVERED Dead No boring Number | Alive boring Number | Alive boring Number | Unrecovered larvae Number |
|---|---|---|---|---|---|---|---|
| Treated | 100 | | 160 | 10 | 0 | 0 | 0 |
| | 100 | | 160 | 10 | 0 | 0 | 0 |
| | 100 | | 160 | 10 | 0 | 0 | 0 |
| Untreated control | — | — | — | 0 | 0 | 10 | 0 |
| | — | — | — | 0 | 0 | 10 | 0 |
| Solvent control | — | — | — | — | — | — | — |

It is intended that the present invention cover modifications and variations which, after reading this disclosure, may be readily apparent to the skilled artisan; for example, the use of other fungicides, stabilizers, insecticides, diluents, emulsifiers, wetting agents, organic-chemical binders or fixing agents which may be employed to yield equivalent results.

What is claimed is:

1. An aqueous composition for preserving wood and wood materials comprising:
    (a) a first fungicide ranging from about 0.1 to about 2.0% by weight of said composition wherein said first fungicide is selected from the group consisting of α-[[2-(4-chlorophenyl)ethyl]-α-(1,1-dimethylethyl)-1H-1,2,4-triazol-1-ethanol and 1-[[2-(2,4-dichlorophenyl-4-propyl-1,3dioxolan-2-yl}methyl]-1H-1,2,4-triazole;
    (b) a second fungicide, said fungicide being a fungicidal carbamate ranging from about 0.2 to about 2.3% by weight of said composition wherein said second fungicide is selected from the group consisting of 3-iodo-2-propynylbutyl carbamate and methyl benzimidazol-2-ylcarbamate;
    (c) a stabilizer ranging from about 1.0 to about 5.0% by weight of said composition wherein said stabilizer is 2,2,4-trimethyl-1,3-pentadiol monoisobutyrate; and
    (d) a diluent comprising at least about 89% by weight of said composition.

2. The aqueous composition of claim 1 wherein said first fungicide ranges from about 0.8 to about 1.5% by weight of said composition.

3. The aqueous composition of claim 1 wherein said second fungicide ranges from about 0.3 to about 1.2% by weight of said composition.

4. The aqueous composition of claim 1 wherein said stabilizer ranges from about 2.0 to about 3.0% by weight of said composition.

5. The aqueous composition of claim 1 wherein said diluent comprises at least about 96% by weight of said composition.

6. The composition of claim 1 further comprising an insecticide ranging from about 0.002 to about 0.8% by weight of said composition, said insecticide selected from the group consisting of cyano-(4-fluoro-3-phenoxyphenyl) methyl 3- (2,2-dichloroethenyl)-2,2-dimethylcyclopropanecarboxylate, (±)α-cyano-3-phenoxybenzyl (±)-cis,trans-3-(2,2-dichlorovinyl)-2,2-dimethylcyclopropanecarboxylate, (S)-α-cyano-3-phenoxybenzyl (1R,3R)-3-(2,2-dibromovinyl)-2,2-dimethylcyclopropanecarboxylate and 3-phenoxybenzyl (±)-cis,-trans-3-(2,2-dichlorovinyl)-2,2-dimethylcyclopropanecarboxylate.

7. The composition of claim 6 further comprising a second insecticide selected from the group consisting of dimethyl(phenyl)silylmethyl 3-phenoxybenzyl ether and dimethyl(phenyl)silylmethyl 2-phenoxy-6-pyridylmethyl ether.

8. The composition of claim 1 further comprising an insecticide selected from the group consisting of dimethyl(phenyl)silylmethyl 3-phenoxybenzyl ether and dimethyl(phenyl)silylmethyl 2-phenoxy-6-pyridylmethyl ether.

9. The composition of claim 8 wherein said dimethyl(phenyl)silylmethyl 3-phenoxybenzyl ether is dimethyl(4-ethoxyphenyl)silylmethyl 3-phenoxybenzyl ether.

10. The composition of claim 8 wherein said dimethyl(phenyl)silylmethyl 2-phenoxy-6-pyridylmethyl ether is dimethyl(4-ethoxyphenyl)silylmethyl 2-phenoxy-6-pyridylmethyl ether.

11. The composition of claim 1 wherein said diluent is an organic solvent.

12. The composition of claim 11 wherein said solvent is polar.

13. The composition of claim 11 wherein said solvent is nonpolar.

14. The composition of claim 1 further comprising an emulsifier.

15. The composition of claim 14 wherein said emulsifier is an ethoxylated nonylphenol.

16. The composition of claim 1 further comprising a binder.

17. The composition of claim 16 wherein said binder is either an alkyd resin or a drying vegetable oil.

18. The composition of claim 16 wherein said binder is a synthetic resin selected from the group consisting of a methylacrylate/n-butylacrylate copolymer, a styrene/acrylic ester copolymer, or a polyvinyl versatate.

19. The composition of claim 1 further comprising a fixing agent.

20. The composition of claim 1 further comprising a wetting agent.

21. A method of preserving wood or wood materials comprising applying to said wood or wood material an effective amount of a composition according to claim 1.

* * * * *